(12) United States Patent
Gupta et al.

(10) Patent No.: US 10,074,028 B2
(45) Date of Patent: Sep. 11, 2018

(54) REAL-TIME DIET ASSESSMENT AND FOOD IDENTIFICATION USING THERMAL IMAGING

(71) Applicants: Sandeep Gupta, Phoenix, AZ (US);
Ayan Banerjee, Mesa, AZ (US)

(72) Inventors: Sandeep Gupta, Phoenix, AZ (US);
Ayan Banerjee, Mesa, AZ (US)

(73) Assignee: ARIZONA BOARD OF REGENTS ON BEHALF OF ARIZONA STATE UNIVERSITY, Scottsdale, AZ (US)

( * ) Notice: Subject to any disclaimer, the term of this patent is extended or adjusted under 35 U.S.C. 154(b) by 0 days.

(21) Appl. No.: 15/298,581

(22) Filed: Oct. 20, 2016

(65) Prior Publication Data
US 2017/0109599 A1   Apr. 20, 2017

Related U.S. Application Data

(60) Provisional application No. 62/243,735, filed on Oct. 20, 2015.

(51) Int. Cl.
| | |
|---|---|
| *G06K 9/00* | (2006.01) |
| *G06K 9/46* | (2006.01) |
| *G06T 7/90* | (2017.01) |
| *G09B 19/00* | (2006.01) |

(52) U.S. Cl.
CPC .............. *G06K 9/4652* (2013.01); *G06T 7/90* (2017.01); *G06K 2209/17* (2013.01); *G06T 2207/10024* (2013.01); *G06T 2207/10048* (2013.01)

(58) Field of Classification Search
CPC .................................... G06K 9/00; G06T 7/00
USPC ............. 382/110; 426/76, 111, 125; 434/127
See application file for complete search history.

(56) References Cited

U.S. PATENT DOCUMENTS

| | | | | |
|---|---|---|---|---|
| 8,363,913 | B2* | 1/2013 | Boushey | G06K 9/00 128/921 |
| 9,095,147 | B2* | 8/2015 | Hjalmarsson | A22C 17/0086 |
| 2004/0260513 | A1* | 12/2004 | Fitzpatrick | G06Q 10/06 702/182 |

OTHER PUBLICATIONS

S. Ba, S. JC, J. WPT et al., "Diet, nutrition and the prevention of excess weight gain and obesity," Public health nutrition, vol. 7, No. 1a, pp. 123-146, 2004.
C. for Disease Control and Prevention, "Maps of trends in diagnosed diabetes and obesity," Aug. 2012, accessed: Jul. 10, 2015. [Online]. Available: http://www.cdc.gov/Diabetes/statistics/slides/maps diabetesobesity trends.pdf.

(Continued)

*Primary Examiner* — Abolfazl Tabatabai
(74) *Attorney, Agent, or Firm* — Michael Best & Friedrich LLP

(57) ABSTRACT

Systems and methods are described for automatically identifying a food item. A color image and a thermal image are received by an electronic processor with a first food item in the field of view of both the color image and the thermal image. The electronic processor identifies a region of pixels in the color image that corresponds to the first food item based at least in part on a temperature intensity of the pixels in the identified region of pixels relative to other pixels in the thermal image. At least one feature is extracted from the identified region of pixels in the color image corresponding to the first food item and the electronic processor automatically identifies a type of food corresponding to the first food item based at least in part on the at least extracted feature.

18 Claims, 8 Drawing Sheets

(56) References Cited

OTHER PUBLICATIONS

R. C. Baker and D. S. Kirschenbaum, "Weight control during the holidays: highly consistent self-monitoring as a potentially useful coping mechanism." Health Psychology, vol. 17, No. 4, p. 367, 1998.
R. C. Baker, "Self-monitoring may be necessary for successful weight control," Behavior Therapy, vol. 24, No. 3, pp. 377-394, 1993.
T. L. Burrows, R. J. Martin, and C. E. Collins, "A systematic review of the validity of dietary assessment methods in children when compared with the method of doubly labeled water," Journal of the American Dietetic Association, vol. 110, No. 10, pp. 1501-1510, 2010.
C. M. Champagne, G. A. Bray, A. A. Kurtz, J. B. R. Monteiro, E. Tucker, J. Volaufova, and J. P. Delany, "Energy intake and energy expenditure: a controlled study comparing dietitians and non-dietitians," Journal of the American Dietetic Association, vol. 102, No. 10, pp. 1428-1432, 2002.
J. R. Hebert, C. B. Ebbeling, C. E. Matthews, T. G. Hurley, M. Yunsheng, S. Druker, and L. Clemow, "Systematic errors in middle-aged women's estimates of energy intake: comparing three self-report measures to total energy expenditure from doubly labeled water," Annals of epidemiology, vol. 12, No. 8, pp. 577-586, 2002.
J.-S. Shim, K. Oh, and H. C. Kim, "Dietary assessment methods in epidemiologic studies," Epidemiology and health, vol. 36, 2014.
K. Wakai, "A review of food frequency questionnaires developed and validated in japan," Journal of epidemiology, vol. 19, No. 1, pp. 1-11, 2009.
K. Poslusna, J. Ruprich, J. H. de Vries, M. Jakubikova, and P. van't Veer, "Misreporting of energy and micronutrient intake estimated by food records and 24 hour recalls, control and adjustment methods in practice," British Journal of Nutrition, vol. 101, No. S2, pp. S73-S85, 2009.
J. R. Pleis, J. W. Lucas, and B. W. Ward, "Summary health statistics for us adults: National health interview survey, 2008." Vital and health statistics. Series 10, Data from the National Health Survey, No. 242, pp. 1-157, 2009.
T. A. Wadden, K. D. Brownell, and G. D. Foster, "Obesity: responding to the global epidemic." Journal of consulting and clinical psychology, vol. 70, No. 3, p. 510, 2002.
C. Rother, V. Kolmogorov, and A. Blake, "Grabcut: Interactive foreground extraction using iterated graph cuts," ACM Transactions on Graphics (TOG), vol. 23, No. 3, pp. 309-314, 2004.
N. Dalai and Triggs, "Histograms of oriented gradients for human detection," in Computer Vision and Pattern Recognition, 2005. CVPR 2005. IEEE Computer Society Conference on, vol. 1. IEEE, 2005, pp. 886-893.
B. S. Manjunath and W.-Y. Ma, "Texture features for browsing and retrieval of image data," Pattern Analysis and Machine Intelligence, IEEE Transactions on, vol. 18, No. 8, pp. 837-842, 1996.
A. Illner, H. Freisling, H. Boeing, I. Huybrechts, S. Crispim, and N. Slimani, "Review and evaluation of innovative technologies for measuring diet in nutritional epidemiology," International journal of epidemiology, vol. 41, No. 4, pp. 1187-1203, 2012.
H. Henriksson, S. E Bonn, A. Bergstr¨om, K. B¨alter, O. B¨alter, C. Delisle, E. Forsum, and M. L¨of, "A new mobile phone-based tool for assessing energy and certain food intakes in young children: A validation study," JMIR mHealth and uHealth, vol. 3, No. 2, 2015.
J. R. Shapiro, T. Koro, N. Doran, S. Thompson, J. F. Sallis, K. Calfas, and K. Patrick, "Text4diet: a randomized controlled study using text messaging for weight loss behaviors," Preventive medicine, vol. 55, No. 5, pp. 412-417, 2012.
M.-Y. Chen, Y.-H.Yang, C.-J. Ho, S.-H. Wang, S.-M. Liu, E. Chang, C.-H. Yeh, and M. Ouhyoung, "Automatic Chinese food identification and quantity estimation," in SIGGRAPH Asia 2012 Technical Briefs. ACM, 2012, p. 29.
P. Pouladzadeh, P. Kuhad, S. V. B. Peddi, A. Yassine, and S. Shirmohammadi, "Mobile cloud based food calorie measurement," in Multimedia and Expo Workshops (ICMEW), 2014 IEEE International Conference on. IEEE, 2014, pp. 1-6.
P. Pouladzadeh, S. Shirmohammadi, and A. Yassine, "Using graph cut segmentation for food calorie measurement," in Medical Measurements and Applications (MeMeA), 2014 IEEE International Symposium on. IEEE, 2014, pp. 1-6.
P. Pouladzadeh, S. Shirmohammadi, A. Bakirov, A. Bulut, and A. Yassine, "Cloud-based svm for food categorization," Multimedia Tools and Applications, pp. 1-18, 2014.
Y. Matsuda, H. Hoashi, and K. Yanai, "Recognition of multiple-food images by detecting candidate regions," in Multimedia and Expo (ICME), 2012 IEEE International Conference on. IEEE, 2012, pp. 25-30.
D. H. Ballard, "Generalizing the hough transform to detect arbitrary shapes," Pattern recognition, vol. 13, No. 2, pp. 111-122, 1981.
P. Arbelaez, M. Maire, C. Fowlkes, and J. Malik, "Contour detection and hierarchical image segmentation," Pattern Analysis and Machine Intelligence, IEEE Transactions on, vol. 33, No. 5, pp. 898-916, 2011.
M. Haghighat, S. Zonouz, and M. Abdel-Mottaleb, "Identification using encrypted biometrics," in Computer Analysis of Images and Patterns. Springer, 2013, pp. 440-448.
Q. Wang, "Kernel principal component analysis and its applications in face recognition and active shape models," arXiv preprint arXiv:1207.3538, 2012.
C.-C. Chang and C.-J. Lin, "Libsvm: A library for support vector machines," ACM Transactions on Intelligent Systems and Technology (TIST), vol. 2, No. 3, p. 27, 2011.
Object recognition from local scale-invariant features. Lowe, D.G. s.l. : IEEE conference on Computer Vision, 1999.
A food image recognition system with multiple kernel learning. Joutou, T., Yanai, K. s.l. : IEEE International Conference on Image Processing, 2009.
Image recognition of 85 food categories by feature fusion. Hoashi, H., Joutou, T., and Yanai, K. s.l. : IEEE International Symposium in Multimedia, 2010.
Real-time mobile recipe recommendation system using food ingredient recognition. Maruyama, T., Kawano, Y., and Yanai, K. s.l. : In Proceedings of the 2nd ACM international workshop on Interactive multimedia on mobile and portable devices, 2012.
Real-time mobile food recognition system. Kawano, Y., Yanai, K. s.l. : IEEE proceedings in Computer Vision and Pattern Recognition Workshops, 2013.
Food Image Analysis: Segmentation, Identification and Weight Estimation. Ye He, Chang Xu, Nitin Khanna, Carol J. Boushey and Edward J. Delp. s.l. : IEEE International Conference on Multimedia and Expo, 2013.
Food recognition using statistics of pairwise local features. Yang, Shulin, et al., et al. s.l. : IEEE Conference on Computer Vision and Pattern Recognition , 2010.
Segmentation and recognition of multi-food meal images for carbohydrate counting. Anthimopoulos, M., et al., et al. s. l. : IEEE 13th International Conference on Bioinformatics and Bioengineering, 2013.
The Effect of Electronic Self-Monitoring on Weight Loss and Dietary Intake: A Randomized Behavioral Weight Loss Trial. Lora E. Burke, Molly B. Conroy, Susan M. Sereika, Okan U. Elci, Mindi A. Styn, Sushama D. Acharya, Mary A. Sevick, Linda J. Ewing, and Karen Glanz. 2, s.l. : Obesity, A Research Journal, 2012, vol. 19.
Lee, J., Banerjee, A., & Gupta, S. K. (Mar. 2016). MT-Diet: Automated smartphone based diet assessment with infrared images. In Pervasive Computing and Communications (PerCom), 2016 IEEE International Conference on (pp. 1-6). IEEE.
Kun, L., Lei, G., Huihui, L., & Jingsong, C. (2009). Fusion of infrared and visible light images based on region segmentation. Chinese Journal of Aeronautics, 22(1), 75-80.
Singh, S., Gyaourova, A., Bebis, G., & Pavlidis, I. (Apr. 2004). Infrared and visible image fusion for face recognition. In Proceedings of SPIE (vol. 5404, pp. 585-596).

(56) References Cited

OTHER PUBLICATIONS

Corias, E., Santamaria, J., & Miravet, C. (2000). A Segment-based Registration Technique for Visual-IR Images. Optical Engineering, 39(1), 282-289.

* cited by examiner

Segmented Image (Output of ROF)

Segmented Color Image (Output of HIS)

Segmented Thermal Image (Output of WMM)

REAL-TIME DIET ASSESSMENT AND FOOD IDENTIFICATION USING THERMAL IMAGING

CORRESPONDING APPLICATIONS

This application claims the benefit of U.S. Provisional Application No. 62/243,735, filed Oct. 20, 2015, entitled "REAL-TIME DIET ASSESSMENT USING THERMAL IMAGE OF FOOD AND GESTURE ANALYSIS," the entire contents of which are incorporated herein by reference.

BACKGROUND

Diet monitoring is an important intervention factor in obesity, which affects over one-third of US adults. Some obesity research has shown that dietary monitoring can significantly help people lose weight. Automated diet monitoring and caloric intake prediction might also provide an effective intervention for chronic diseases such as obesity and diabetes that affect nearly one-third of US adults with a combined estimated economic cost of $392 Billion.

The present invention relates to systems and methods for automatically identifying food items and automated diet assessment.

SUMMARY

Diet is an important factor in obesity, which affects over one third of US adults. Some obesity research has shown that dietary monitoring can significantly help people lose weight. Self-monitoring techniques for diet, such as manual paper-based records (food diaries) and 24-hour dietary recalls that assess the amount and type of food eaten, might be helpful. However, these techniques suffer from three important drawbacks: a) adherence to self-monitoring for the prescribed period of intervention is low (nearly 63%), b) self-reporting is prone to underreporting, especially in individuals with obesity by amounts ranging from 20%-50%, and c) recall error while reporting food intake. Further, in self-reported dietary assessment, where a 0.5 to 0.7 correlation with actual intake would be considered good; many studies have found a 0.4 correlation with self-reported dietary assessment and intake. The misclassification of caloric intake and nutrient profiles tends to be differential based on weight status and/or overall energy intake. Moreover, after a weight loss program involving diet self-monitoring there is a high rate of relapse.

In various embodiments, systems and methods described in this disclosure provide an automated diet monitoring system that uses images/data from a thermal sensor to recognize food types. In some embodiments, a user can take images in both infrared and visual spectrum, which are then used to identify types of food on a plate. Some embodiments provide: i) automated food segmentation, without any input from the user, ii) automated food identification, iii) automated food quantity estimation, using gesture recognition, iv) privacy preservation, i.e., does not depend on crowd-sourcing food intake information, v) personalization, i.e., can be configured to eating habits of individuals, vi) network independence, i.e., does not always need wireless communication and can work locally in the smartphone, and vii) capacity to provide real time feedback on caloric intake.

In some embodiments, the food identification system captures an image of a food plate in both infrared (thermal) and visual (color) spectra through a thermal camera interfaced with a smart phone (or other portable computing device) and a visual (color) camera built into the smart phone. With hot food, the food plate is generally cooler than the food itself; as a result, the thermal image gives a better opportunity to accurately segment different food portions on a plate. Further, the same amount of heat will yield different temperature increases for different food items. Thus, even if two food types are mixed, a thermal image can distinguish between them. The segmented area is then applied to the color image after proper rotation and scaling guided by two reference points in the image. Unwanted portions of the food plate in segmentations are further removed using a process such as, for example, the GrabCut method. In some embodiments, color histogram-based analysis of each segment is used to determine the actual number of food items on the plate and the area covered by them. The food segments from both the thermal and color images are used to extract one or more of the following features, a) relative temperature difference of each food item with respect to food plate from the thermal image, b) color map, c) histogram of gradients, and d) texture information from the color image. These features are then provided as input to a support vector machine (SVM) based classifier to match to a pre-existing food database and extract the type of food.

In one embodiment, the invention provides a method of identifying a food item. A color image and a thermal image are received by an electronic processor with a first food item in the field of view of both the color image and the thermal image. The electronic processor identifies a region of pixels in the color image that corresponds to the first food item based at least in part on a temperature intensity of the pixels in the identified region of pixels relative to other pixels in the thermal image. At least one feature is extracted from the identified region of pixels in the color image corresponding to the first food item and the electronic processor automatically identifies a type of food corresponding to the first food item based at least in part on the at least extracted feature.

In another embodiment, the invention provides a food identification system including a color camera, a thermal camera, and an electronic processor. The electronic processor is configured to receive a color image from the color camera and a thermal image from the thermal camera. A first food item is in the field of view of both the thermal image and the color image. The electronic processor identifies a region of pixels in the color image corresponding to the first food item based at least in part on a temperature intensity of the pixels in the identified region of pixels relative to other pixels in the thermal image. The electronic processor then extracts at least one feature from the identified region of pixels in the color image corresponding to the first food item and automatically identifies a type of food corresponding to the first food item based at least in part on the at least one extracted feature.

In still other embodiments, the invention provides a method of identifying a food item. A color image and a thermal image are received with a plurality of food items positioned in the field of view of both the color image and the thermal image. A scale and orientation of the thermal image is calibrated to align with the field of the color image. An electronic processor identifies a first region of interest in the color image corresponding to a potential food item of the plurality of food items based at least in part on an edge finding routine applied to the color image. The electronic processor also identifies a second region of pixels in the thermal image corresponding to a potential food item based at least in part on a temperature intensity of the pixels in the identified second region of pixels relative to other pixels in the thermal image. The electronic processor then determines whether the first region of pixels in the color image corresponds to a first food item of the plurality of food items based at least in part on an alignment of at least some of the pixels in the first region of pixels in the color image with the second region of pixels in the thermal image.

Other aspects of the invention will become apparent by consideration of the detailed description and accompanying drawings.

DETAILED DESCRIPTION

Before any embodiments of the invention are explained in detail, it is to be understood that the invention is not limited in its application to the details of construction and the arrangement of components set forth in the following description or illustrated in the following drawings. The invention is capable of other embodiments and of being practiced or of being carried out in various ways.

Figure 1:
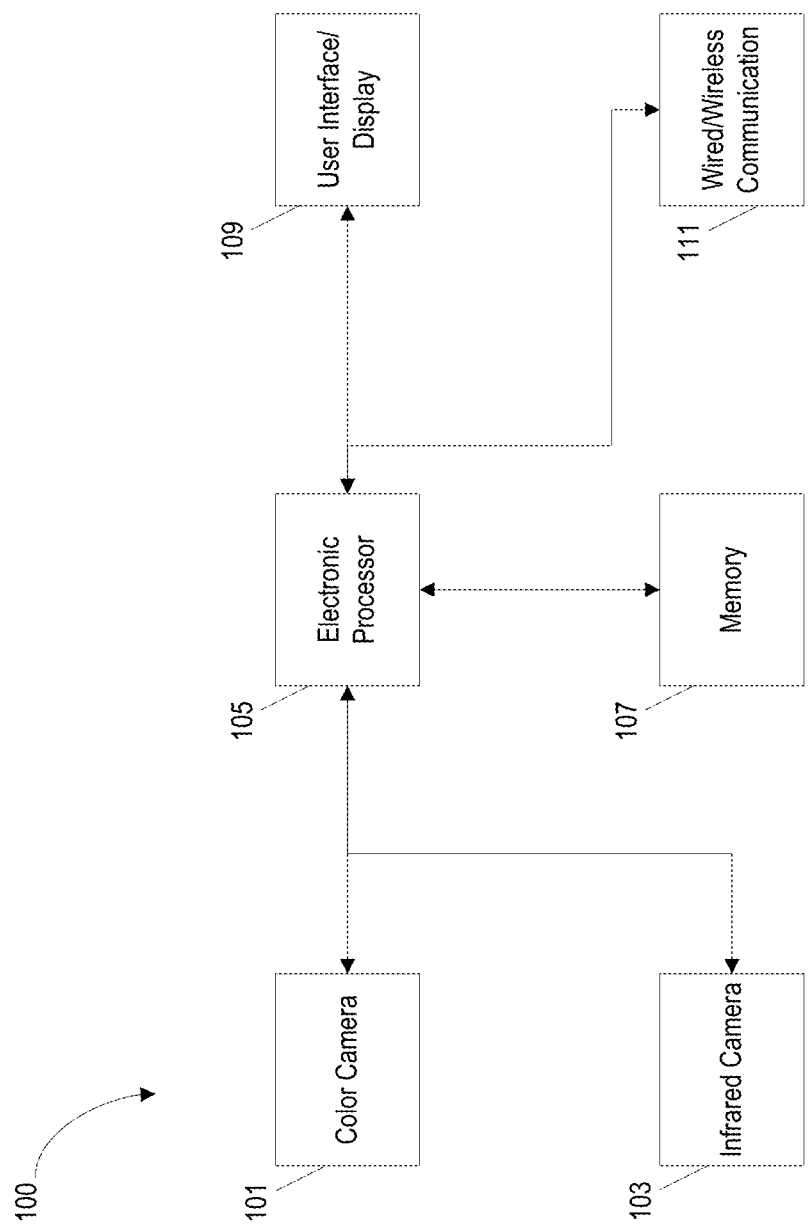
FIG. 1 is a block diagram of a food identification system according to one embodiment.

FIG. 1 illustrates an example of a food identification system 100. A color camera 101 and an infrared camera 103 (or another type of thermal imaging device) are communicatively coupled to an electronic processor 105. The electronic processor 105 is coupled to a non-transitory computer-readable memory 107. The memory 107 stores data including, for example, a food identification data base (as discussed in further detail below) and instructions that are executed by the electronic processor to provide the functionality of the food identification system as discussed in further detail below. In various implementations, the electronic processor 105 and the memory 107 may be provided as one or more separate components/modules. For example, in some implementations, a single microcontroller might serve as both the electronic processor 105 and the memory 107 while, in other implementations, multiple different logic components may be used to implement the functionality of the electronic processor 105 as described below. Similarly, in some embodiments, the memory 107 may be implemented as multiple separate memory modules or components.

The electronic processor 105 is also communicatively coupled to a user interface/display 109 configured to provide output information to a user and to receive input commands. The electronic processor 105 is also communicatively coupled to a wired or wireless communication module for communication between the food identification system 100 and other external systems or databases.

In some implementations, the food identification system 100 is implemented as a smart phone or other portable computing device (e.g., a tablet computer). The user interface/display 109 is provided as the touchscreen display of the smart phone, the electronic processor 105 and memory 107 are provided as the processor and memory of the smartphone, and the wired/wireless communication module 111 is provided as one or more of the smart phone's wireless communication mechanisms including, for example, the 4G LTE cellular, Bluetooth, or WiFi communication. The color camera 101 may similarly be provided as the built-in camera of the smart phone. The infrared/thermal camera may also be provided as a feature of the smart phone's built-in camera system, a separate built-in sensor of the smart phone, or as a separate device component that is configured to capture thermal images and to communicate with the smart phone via a wired or wireless communication interface.

Figure 2:
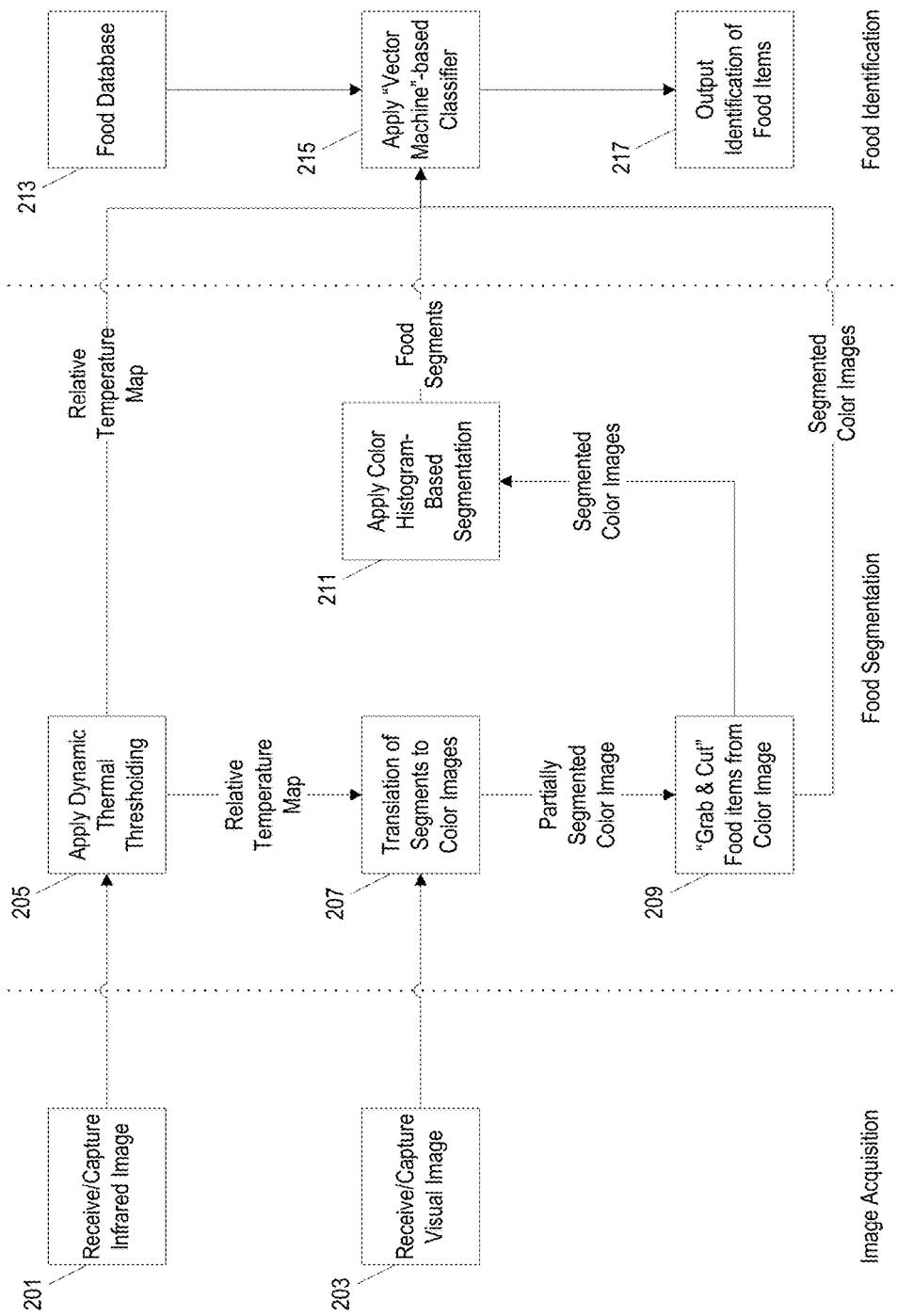
FIG. 2 is a flowchart of a method for identifying one or more food items based on a thermal image and a visual image using the food identification system of FIG. 1.

FIG. 2 illustrates a first example of a three-stage process for automatically identifying food items on a plate using the food identification system of FIG. 1. The three stages include (1) image acquisition, (2) food segmentation, and (3) food identification. During the image acquisition stage, a thermal/infrared image of a food plate is captured by the infrared/thermal camera 103 (step 201) and a visual/color image of the food plate is captured by the color camera 101 (step 203).

During the food segmentation stage, dynamic thermal thresholding (step 205) is applied to the captured thermal image to generate a relative temperature map. Segments identified by the thermal thresholding are then translated to segments of the color images (step 207) to generate a partially segmented color image. A segmentation refining process (such as, for example, a "GrabCut" routine as discussed further below) is then applied (step 209) to produce a fully segmented color images. Color histogram-based segmentation is then applied to identify individual food segments (step 211).

During the food identification stage, data from a food item database 213 is used to identify the individual food items on the plate based on the relative temperature map, the segmented color images, and the separated food segments produced during the food segmentation stage. In some implementations, a vector machine-based classifier is applied to identify each particular food item (step 215). In some implementations, once an individual food item is identified, the identification is output to the user on the user interface/display 109 (step 217) and the user is asked to confirm that the food items have been correctly identified. In other implementations, the identity of each food item in the image is stored to the memory 107 or communicated to a remote server for storage and processing. In some implementations, the image is further processed to estimate a quantity or amount of the food item on the plate, calculate dietary information (e.g., calorie count), and automatically store the dietary information to an electronic record that tracks dietary information for an individual user.

Figure 3:
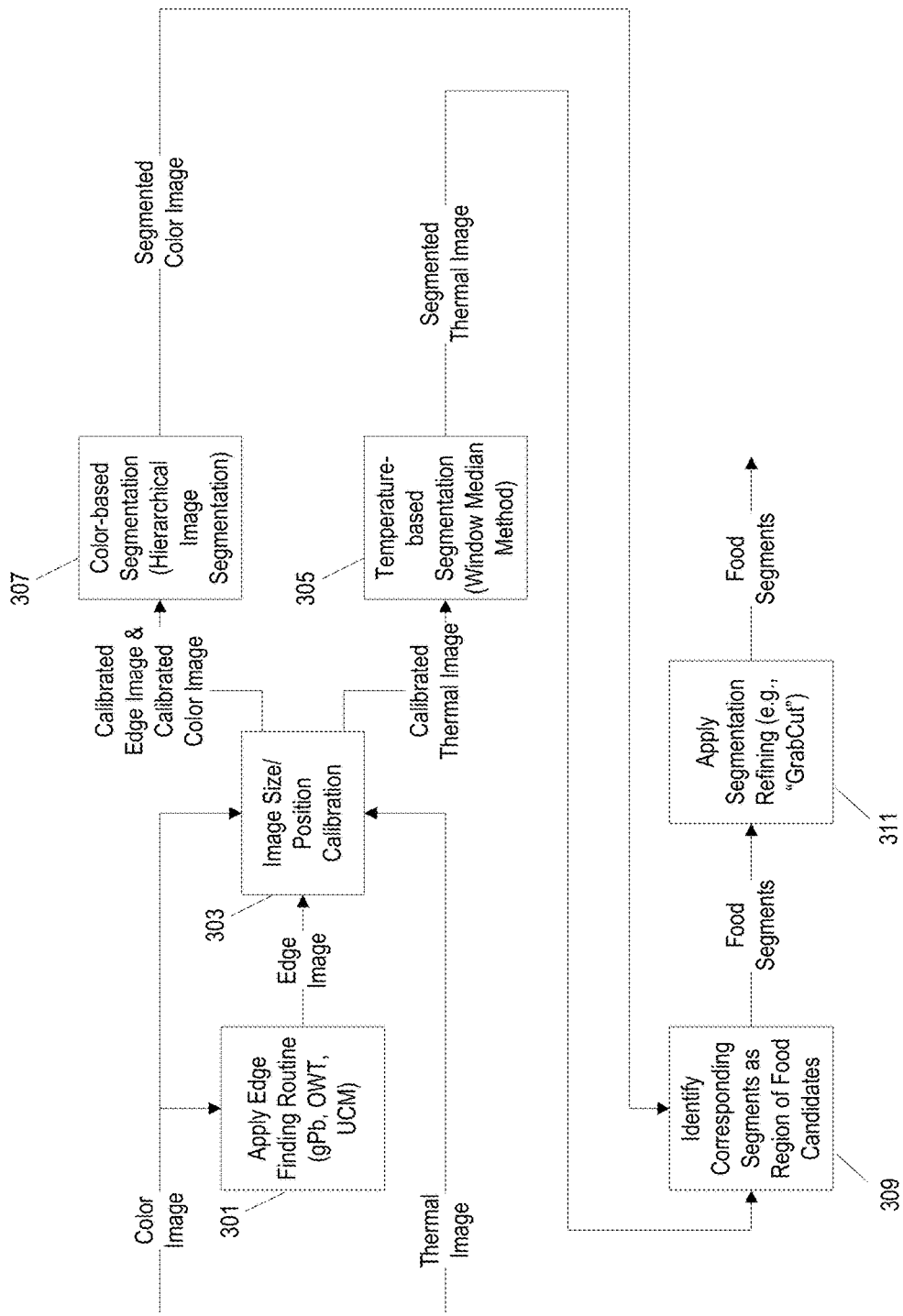
FIG. 3 is a flowchart of a method for food item segmentation using the system of FIG. 1.
Figure 6:
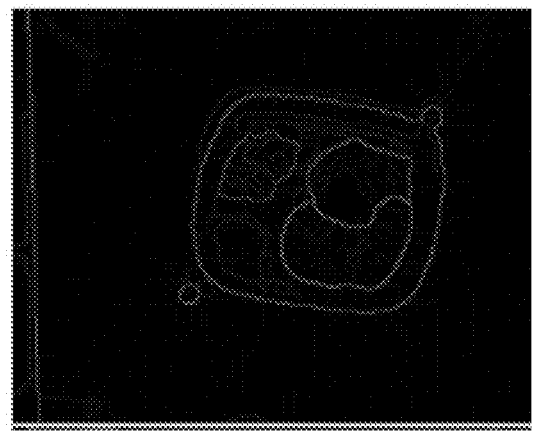
FIG. 6 is an example of an edge image generated during the food item segmentation process of FIG. 3.

FIG. 3 illustrates another, more detailed method for performing the food segmentation stage. Again, a color image is received (for example, from the built-in camera of a smart phone) and a thermal image is received (for example, from a thermal imaging device connected to the smart phone). In this example, the thermal image is a gray scale image where the intensity of each pixel is directly proportional to a temperature.

An edge finding routine is applied to the color image (step 301) to generate an "edge image." In this example, the edge finding routine includes a gPb-OWT-UCM (Global Probability of Boundary—Oriented Watershed Transform—Ultrameric Contour Map) algorithm. An image size/position calibration is then performed using the color image, the edge image, and the thermal image (step 303). This calibration process corrects for differences in resolution, size, and position in each of the three images and produces a calibrated color image, a calibrated edge image, and a calibrated thermal image that all have the same resolution and pixel-by-pixel coordinate positions. If the color camera and the thermal camera are both fixedly coupled to each other (e.g., both embedded in a smart phone or fixedly attached to the same device housing), then the calibration process only needs to be performed once (or periodically, but not on every use).

In some implementations, the calibration process (step 303) automatically identifies common features that are in different image types, registers the common features to each other, and proceeds to rotate/rescale the images until the images are aligned. In one specific embodiment, a line is superimposed on each image based on an identified target and serves as the "standard" subject for the calibration process. More specifically, a line is drawn based on an identified image target in the color image and the thermal image and the lines are then calibrated pixel-by-pixel by comparing the slope and size of the line in each image type. To ensure that the "lines" that are generated in each image type are the "same" and can be used as a reliable calibration standard, a "target" may be placed on or near the plate or food item to be captured in both the thermal image and the color image. For example, a bottle cap containing cold water can be positioned at different locations near the food. Due to the relative cold temperature of the water in the bottle cap and the circular shape of the bottle cap itself, the bottle cap can be identified in both the thermal image and the color image. The calibration line is then added to each image type linking the center of the circular objects (i.e., the bottle caps) automatically identified in both image types.

One specific type of circular object detection technique that might be used to identify the location of the circular bottle cap target in both the visual image and the thermal image is a Hough Transform. Using an edge image (such as generated in step 301) as an input to the Hough Transform routine results in improved performance and accuracy as compared to a raw color image. Threshold values for the edge image and the thermal image can be tuned to increase the accuracy of finding the circular object candidates. For example, a threshold value of 25 of 255 can be used for the edge image and a threshold value of 5 for the thermal image (based on the assumption that the cold water in the bottle cap is the lowest temperature item in the thermal image).

A straight line that passes through the center pixel positions of the bottle cap target in the thermal image and the edge image is obtained by the equation:

$$y - y_1 = \frac{y_2 - y_1}{x_2 - x_1}(x - x_1) \tag{1}$$

where $x_1$ and $y_1$ are a XY-coordinate center pixel position of the first identified target and $x_2$ and $y_2$ is the XY-coordinate center pixel position of the second identified target (if $x_1$ does not equal $x_2$). The slope of this line is used for matching food position pixels in the edge image with the food position pixels in the thermal image.

The slope can be converted to a radian and, thereafter, into a degree $\theta$ using the equations:

$$\text{rad} = \tan^{-1}\left(\frac{y_2 - y_1}{x_2 - x_1}\right) \tag{2}$$

$$\theta = \frac{\text{rad} * 180}{\pi}$$

The thermal image is rotated relative to the edge image based on a difference between the angle $\theta$ for the edge image and the angle $\theta$ for the thermal image.

To adjust for difference in resolution/size of the image types, a Euclidean distance between the centers is calculated for each image type using the equation:

$$\text{dis} = \sqrt{(x_2 - x_1)^2 + (y_2 - y_1)^2} \tag{3}$$

The ratio of the lines' Euclidean distances is then used as a scale size factor to resize the thermal image to match the edge image and the color image.

After completing the appropriate rotation and resizing, the food position pixels of the various different image types will have the same resolution and position. However, the food pixels' indexes in the images may still be unequal. To correct for possible image indexing discrepancies, the edges of all image types are cropped at the center location of the bottle cap. When using this cropping technique as part of the image calibration process, the bottle cap can either be positioned in the upper left corner relative to the food item or the images can be rotated as part of the calibration to position one of the bottle cap targets in the upper left corner so that it can be used as a cropping point.

The output of the calibration process 303 is a calibrated edge image, a calibrated color image, and a calibrated thermal image that all share the same scale, orientation, and pixel indexing. Next, food item location information is extracted from the calibrated thermal image using a temperature-based segmentation process (step 305). Since the thermal image is a gray scale image, a temperature threshold could be used to separate pixels that represent food items from pixels that represent background (i.e., a table or plate) if the food identification system knows the temperature of the background (i.e., the table or the plate).

If the precise temperature of the plate is not known, another method—referred to herein as the "Window Median Method" (WMM)—is applied to determine appropriate threshold values for temperature-based segmentation of the thermal image. For example, if the food identification system is configured to identify food items on a plate that is at a lower temperature than the food items, then the food identification system can be configured to begin application of the WMM by defining a temperature threshold of "remained" pixels in the thermal image (i.e., pixels that do not represent the plate or any food items). This threshold may be determined experimentally or "tuned" for a specific user based on preference and eating habits. If, however, the "remained" pixel threshold is set at 150, the plate temperature can be determined using the equation:

$$rBP(i, j) = \begin{cases} 0, & \text{if thermal}(i, j) < 150 \\ \text{thermal}(i, j), & \text{else} \end{cases} \quad (4)$$

$$W = \begin{bmatrix} rBP(i, j) & rBP(i, j+1) & rBP(i, j+2) \\ rBP(i+1, j) & rBP(i+1, j+1) & rBP(i+1, j+2) \\ rBP(i+2, j) & rBP(i+2, j+1) & rBP(i+2, j+2) \end{bmatrix}$$

$$\text{diff\_mat} = \begin{cases} 0, & \text{if } W \text{ has zero} \\ \text{Max}(W) - \text{Min}(W), & \text{else} \end{cases}$$

$$[x, y] = \text{Index of Max(diff\_mat)}$$

$$CD = \begin{bmatrix} rBP(x, y) & rBP(x, y+1) & rBP(x, y+2) \\ rBP(x+1, y) & rBP(x+1, y+1) & rBP(x+1, y+2) \\ rBP(x+2, y) & rBP(x+2, y+1) & rBP(x+2, y+2) \end{bmatrix}$$

$$T = \text{median}(CD)$$

In Equation (4), a three-by-three window W is applied to the removed remained pixels (rBP) to generate a difference matrix (diff_mat) whose elements are the differential between maximum and minimum values in W. When W has zero intensity, the element is not utilized to find the plate temperature because a zero intensity means that the element is a remained pixel. This mechanism also obtains a pixel position and index of the highest temperature differential in the image as obtained by the maximum value(s) in the diff-mat. The elements of the three-by-three window of [x; y] (CD in Equation (4)) are identified as candidates for the threshold value that will be used to remove pixels corresponding to the plate. This is because the food temperature is assumed to be significantly higher than the temperature of the plate in the image. In some implementations, the threshold value (T) that will be used to identify pixels corresponding to the plate is calculated as the median of the elements in the window CD.

After an appropriate threshold for removing plate pixels is identified using the WMM, the food identification system applies the threshold to remove all of the plate and "remained" pixels leaving only pixels that presumably correspond to food items (i.e., a "segmented thermal image"). However, in some implementations and in some situations, the output of the WMM may still include "salt-and-pepper" noise and some pixels corresponding to food items may have been erroneously removed if the temperature of the food at a certain location is significantly lower compared to the temperature of the rest of the food item(s). To delete "salt-and-pepper" noise in the segmented thermal image, morphology techniques such as "opening and closing" may be employed. To better determine which pixels corresponding to food items may have been erroneously removed in the segmented thermal image, a color-based segmentation mechanism (step 307) is applied to the calibrated color image. In some implementations, the color-based segmentation mechanism includes a Hierarchical Image Segmentation ("HIS") technique and may utilize the calibrated edge image to produce a segmented color image.

The output of the temperature-based segmentation (i.e., the segmented thermal image) and the output of the color-based segmentation (i.e., the segmented color image) are then analyzed to identifying corresponding segments as "region of food" candidates (step 309). First, any "pixel chunks" that are identified by the HIS method (i.e., in the segmented color image) that correspond to "pixel chunks" with the same index (i.e., location) that are identified by the WMM method (i.e., the segmented thermal image) are identified as candidates for "region of food." In some implementations, if a "pixel chunk" identified in the WMM includes at least one pixel that was also identified in the HIS process, then the pixel chunk is identified as a candidate for a "region of food."

After food segments are identified as candidates for "regions of food" (i.e., the output of step 309), these identified regions may still include noise pixels due to shadow (in the color image) and a warmed portion of the plate surrounding a food item (in the thermal image). Furthermore, some food pixels may have been erroneously omitted from the identified regions because the output of the HIS mechanism is an approximate segmentation employing the edge image as an input. To more precisely identify the segmentation of the pixels corresponding to actual food items, a segmentation refining mechanism is applied by the food item identification system (step 311).

In some examples, a "GrabCut" routine is applied as the refining mechanism. GrabCut is an image segmentation method based on graph cuts that generally begins with a specified boundary around an object to be segmented and estimates the color distribution of a target object and of a background using a Gaussian mixture model. This process is applied iteratively until the identified region converges. The regions identified in step 309 as candidates for regions of food are used as the specified boundaries to initiate the GrabCut routine. The GrabCut routine is applied for each of the identified "region of food" candidates meaning that, if three separate areas are identified as candidates in step 309, the GrabCut routine is performed three times. The output of the GrabCut routine is a refined set of one or more food segments that accurately reflects only pixels corresponding to the food items and not to the plate or the background (i.e., remained pixels).

Figure 5:
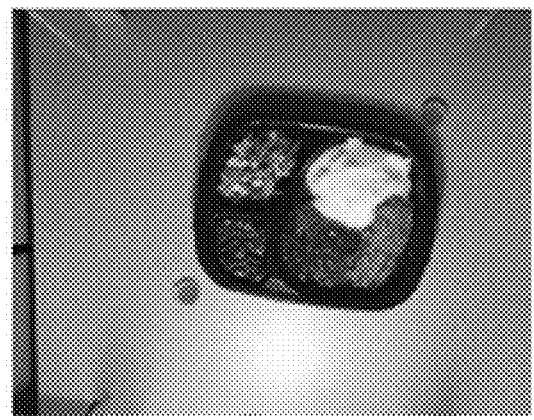
FIG. 5 is an example of a color image captured by the system of FIG. 1.
Figure 4:
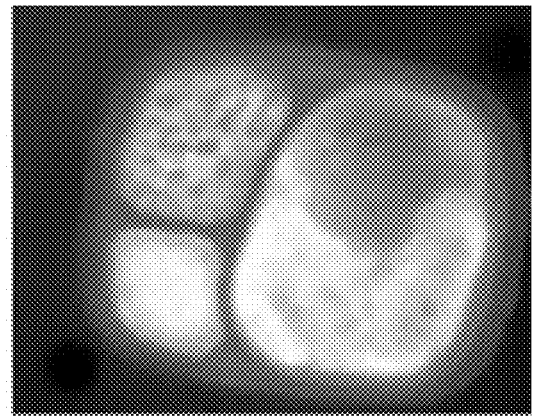
FIG. 4 is an example of a thermal image captured by the system of FIG. 1.
Figure 9:
FIG. 9 is an example of a calibrated color image generated during the food item segmentation process of FIG. 3.

FIGS. 4-13D illustrates an example of a series of images processed according to the food segmentation method of FIG. 3. FIG. 4 shows a thermal image captured by the thermal camera 103 and FIG. 5 shows a color image captured by the color camera 101. The edge finding routine (step 301, FIG. 3) is applied to the color image of FIG. 5 to generate the edge image of FIG. 6. The image size/position calibration routine (step 303, FIG. 3) outputs the calibrated edge image of FIG. 7, the calibrated thermal image of FIG. 8, and the calibrated color image of FIG. 9.

Figure 8:
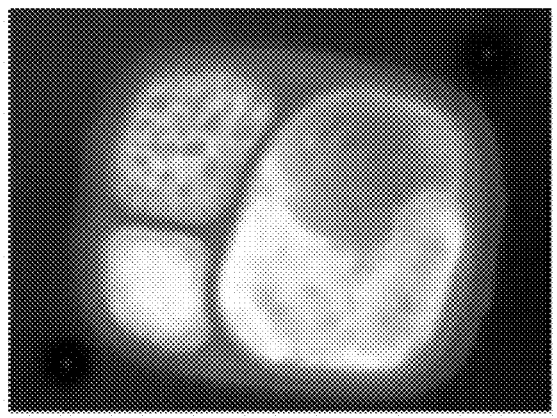
FIG. 8 is an example of a calibrated thermal image generated during the food item segmentation process of FIG. 3.
Figure 7:
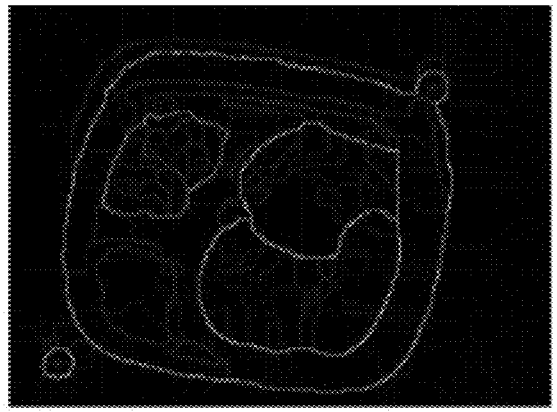
FIG. 7 is an example of a calibrated edge image generated during the food item segmentation process of FIG. 3.
Figure 12:
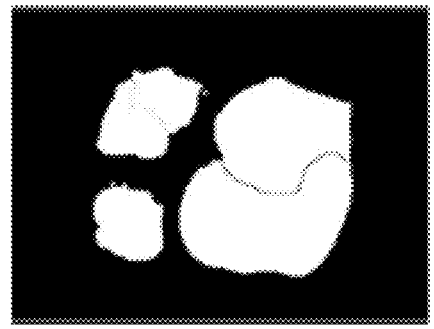
FIG. 12 is an example of a segmented image generated during the food item segmentation process of FIG. 3
Figure 10:
FIG. 10 is an example of a segmented thermal image generated during the food item segmentation process of FIG. 3.

Applying the Window Mean Method (step 305, FIG. 3) to the calibrated thermal image of FIG. 8 generates the segmented thermal image of FIG. 10. Similarly, applying the hierarchical image segmentation routine (step 307, FIG. 3) to the calibrated color image of FIG. 9 produces the segmented color image of FIG. 11. FIG. 12 shows the final segmented image that is generated based on information from both the segmented color image and the segmented thermal image. In the final segmented image of FIG. 12, the four different food items on the plate have been correctly segmented.

Figure 11:
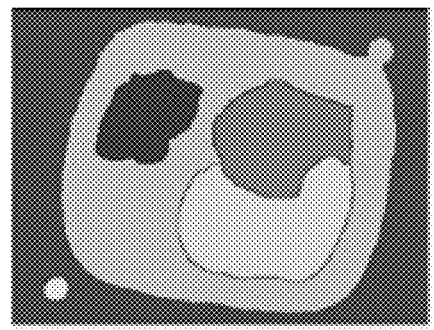
FIG. 11 is an example of a segmented color image generated during the food item segmentation process of FIG. 3.

The example of FIGS. 10-12 illustrates certain limitations of the thermal segmentation method and the color segmentation method individually that are resolved when combined as discussed above. First, as shown in FIG. 10, the segmented thermal image does not include the region of pixels corresponding to the mashed potatoes (in the lower right corner of the plate). This result can occur when the temperature of a particular food item is relatively close to the temperature of the plate as compared to the temperature of the other food items on the plate. Second, as shown in FIG. 11, the segmented color image does not include the region of pixels corresponding to the "brownie" food item (in the upper left corner of the plate). This result can occur when the color of a food item closely resembles the color of the plate. However, because the mashed potatoes food item was correctly identified and segmented in the segmented color image and the brownie food item was correctly identified and segmented in the segmented thermal image, the combined segmented image includes both food items.

In some implementations, the food identification system is configured, based on an assumption that all food items will be contained on the plate, to determine that a segmented group of pixels identified by only one of the color-based segmentation or the temperature-based segmentation (but not both) is indeed a candidate for region of food if pixels within the region have been identified as part of the plate in the other segmentation method. In the example of FIGS. 10-12, a region of pixels corresponding to the mashed potatoes was identified by the color-based segmentation, but not by the thermal-based segmentation. In some embodiments, the food identification system may be configured to identify the region of pixels as a candidate for a "region of food" based only on the color-based segmentation if a median pixel in the region of pixels corresponds to a pixel identified as part of the plate in the thermal-based segmentation. Conversely, a region of pixels corresponding to the brownie was identified by the thermal-based segmentation, but not by the color-based segmentation. In some embodiments, the food identification system is configured to identify a region of pixels as a candidate for a "region of food" based only on the temperature-based segmentation if a defined percentage (e.g., 95%) of the pixels in the identified region of pixels in the segmented thermal image correspond pixels identified as part of the plate in the segmented color image.

Figure 13D:
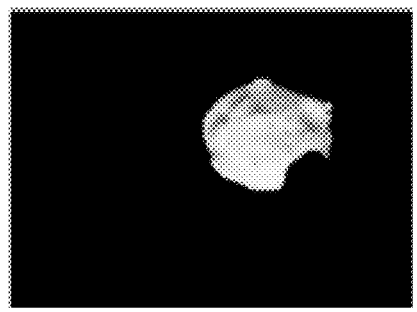
FIGS. 13A, 13B, 13C, and 13D are examples of individual segmented food items identified during the food item segmentation process of FIG. 3.
Figure 13C:
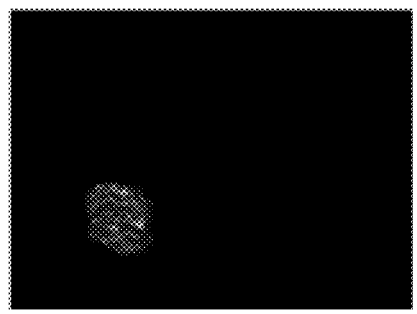
Figure 13B:
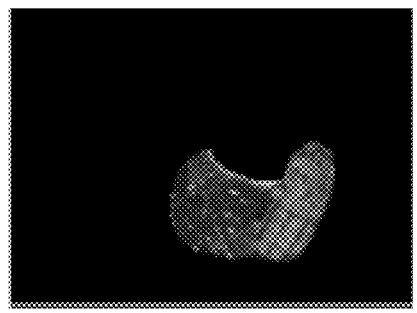
Figure 13A:
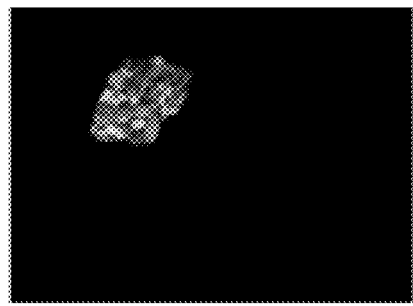

After the GrabCut routine is performed to refine the boundaries of each food segment, each food segment boundary is applied to the color image to provide a color image that includes only pixels identified as corresponding to a single food item. FIG. 13A shows the first food segment (i.e., mixed vegetables) isolated in an output color image. FIG. 13B shows the second food segment (i.e., the meat entrée) isolated in an output color image. FIG. 13C shows the third food segment (i.e., the brownie) isolated in an output color image. FIG. 13D shows the fourth food segment (i.e., the mashed potatoes) isolated in an output color image.

Figure 14:
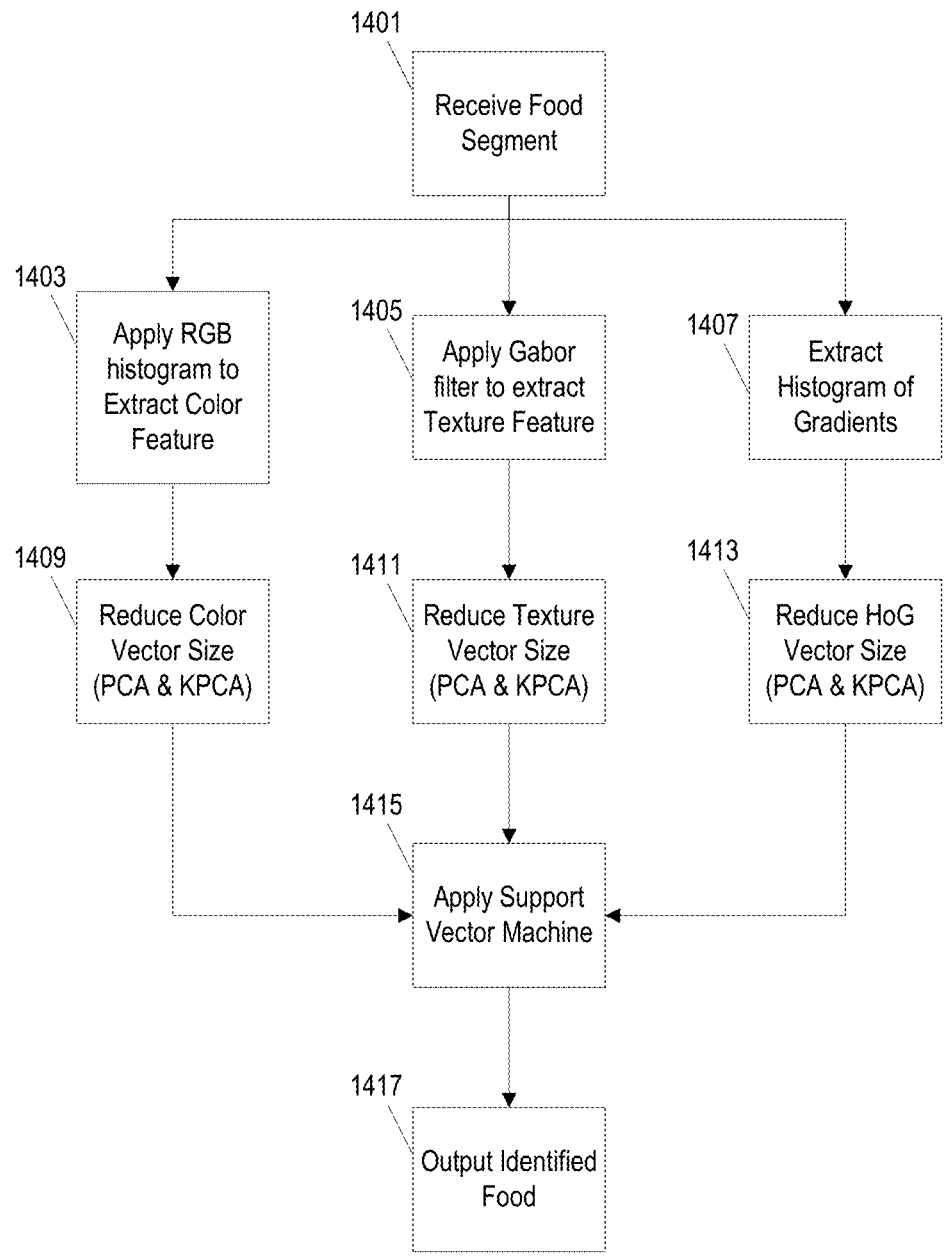
FIG. 14 is a flowchart of a method food item identification based on the output of the food item segmentation process of FIG. 3 using the system of FIG. 1.

After each food item is identified and segmented in the color image using the color and temperature-based processing techniques described above in reference to FIG. 3, the color image of each segmented food item is processed to identify the specific type of food item. FIG. 14 illustrates an example of a method for identifying a food item in a segmented color image by extracting features and classification. A segmented food item is received from the output of the food segmentation stage (step 1401) and, in the example of FIG. 14, three different feature extractions are applied to the food segment.

First, an RGB histogram is applied to extract color features from the color image in the food segment (step 1403). In some implementations, the number of histogram bins used are 32 for red, 32 for green, and 32 for blue so that the size of the resulting color feature vector for the food segment is 32768 (i.e., 32×32×32).

Second, a Gabor filter is applied to extract texture features (step 1405). To ensure that the texture feature extraction is applied primarily to pixels corresponding to the particular food item, the food segment image (e.g., the image of FIG. 13A) is cropped as a rectangle with an upper left corner at the minimum x and minimum y of the food pixels and with a lower right corner at the maximum x and maximum y of the food pixels. In some implementations, after the image is cropped, it is resized/scaled to ensure that the same number of food pixels are used for the texture analysis and, accordingly, so that the size of the food item (i.e., the number of pixels in the image) does not impact the resulting texture feature vector. For example, each food item image can be cropped and scaled to 400 pixels by 400 pixels before applying the Gabor filter to generate a texture feature vector. The size of the texture feature vector is the size of the food image (e.g., 400×400) multiplied by the number of scales and orientations (e.g., 5×8) divided by the row and column downsampling factors (e.g., 4×4) (e.g., a total texture feature vector of size 400,000).

Third, a histogram of gradient ("HoG") feature is extracted from the individual food item segment (step 1407). If each food image is divided as 16 windows and oriented gradients of each window are calculated by 36 bin histograms, then the size of the HoG feature vector is 16×36=576.

The feature vectors are then combined and used, in reference to a food item database, to identify the specific food item in the identified food segment. In some implementations, the feature vectors are combined by simple attachment (i.e., the texture feature vector, the color feature vector, and the HoG feature vector are added to the end of each other). The size of the resulting feature vector can be quite large which, in turn, requires a longer execution time to identify the food item. Therefore, in some implementations, a Principal Component Analysis (PCA) and Gaussian Kernel Principal Component Analysis (KPCA) is applied to the resulting combined feature vector to decrease its size by reducing dimensionality and noise.

However, applying the PCA and KPCA to reduce the vector size after combination of the feature vectors by attachment can cause one individual feature to dominate the resulting combined feature vector. For example, in the scenario described above, where the texture feature vector is added to the end of the color feature vector and the HoG feature vector is then added to the end of the combined vector, reducing the size of the combined feature vector will cause the color feature vector to provide the dominant influence in the resulting reduced and combined feature vector.

Therefore, in the example of FIG. 14, to prevent any individual feature vector in the multiple vector analysis from dominating the value of the combined feature vector, the PCA and KPCA routines are applied separately to the color feature vector (step 1409), to the texture feature vector (step 1411), and to the HoG feature vector (step 1413). After the size of each individual feature vector is reduced (for example, to a size of 100 each), the three feature vectors are combined by attachment (resulting in a combined feature vector size of 300).

The combined feature vector is then used as an input to a data base analysis in order to identify a specific food item that most closely correlates to the color, texture, and HoG of the particular food segment. In some implementations, a machine learning or data mining routine is used to further refine the data base and the food identification mechanism as additional food items are identified. In the example of FIG. 14, a support vector machine (SVM) technique is applied (step 1415) to identified a type of food item in the food item database that most closely corresponds to the features as indicated by the combined feature vector. When the food item is identified, the identification is output (step 1417) to be stored and/or used for further dietary analysis.

The method of FIG. 14 is executed by the food identification system for each individual food segment identified during the food segmentation stage. Therefore, in the example of FIGS. 4-13D, the method of FIG. 14 is executed four times (once for each of the four food segments in FIGS. 13A, 13B, 13C, and 13D). Furthermore, in some implementations, the identification of each food item on a plate is displayed on the screen of the food identification system (e.g., on the screen of the user's smart phone). The user may then be prompted to confirm whether the food items were identified correctly. In implementations that utilize a machine learning mechanism (such as the SVM) to identify individual food items, the food identification system may update the food item database based on the extracted features from correctly identified food items. Furthermore, in some implementations, a user may be prompted to manual identify food items that could not be identified automatically or that were incorrectly identified. The food item database is then updated based on the manual identification in order to improve the ability of the food identification system to accurately identify the particular food item when it is encountered again. In some implementations, extracted features from automatically and manually identified food items are included in a shared food item database (without identifying any specific user/patient) so that data from multiple users can be aggregated to improve the functioning of the automatic food identification system.

In some implementations, after each food item is identified, the system is configured to estimate a quantity or amount of each individual food item in the image and to calculate dietary information based on the type and amount of the food item. This calculated dietary information—including, for example, a calorie count—are then stored to a diet analysis log for the user to track eating patterns and diet compliance.

Thus, the invention provides, among other things, a system and method for automatically identifying food items in a color image using thermal image data of the same food item. Various features and advantages of the invention are set forth in the following claims.

What is claimed is:

1. A method of identifying a food item, the method comprising:
    positioning two identifiable calibration targets near a first food item, the two identifiable calibration targets include a first calibration target and a second calibration target;
    capturing a color image with the first food item and the two identifiable calibration targets within a field of view of the color image;
    capturing a thermal image with the first food item and the two identifiable calibration targets within a field of view of the color image;
    receiving the color image with the first food item in the field of view of the color image;
    receiving the thermal image with the first food item in the field of view of the thermal image;
    defining, by an electronic processor, a line in the thermal image extending from a defined location on the first calibration target to a defined location on the second calibration target;
    defining, by the electronic processor, a line in the color image extending from the defined location on the first calibration target to the defined location on the second calibration target;
    adjusting an orientation and a scale of the thermal image or the color image until a slope and size of the line in the thermal image matches a slope and size of the line in the color image;
    identifying, by the electronic processor, a region of pixels in the color image corresponding to the first food item based at least in part on a temperature intensity of the pixels in the identified region of pixels relative to other pixels in the thermal image;
    extracting at least one feature from the identified region of pixels in the color image corresponding to the first food item; and
    identifying, by the electronic processor, a type of food corresponding to the first food item based at least in part on the at least one extracted feature.

2. The method of claim 1, further comprising:
    analyzing, by the electronic processor, the thermal image to identify a thermal threshold indicative of a difference between a temperature of one or more food items on a plate and a temperature of the plate, wherein the one or more food items on the plate includes the first food item; and
    identifying at least one region of pixels corresponding to the one or more food items on the plate by identifying pixels in the thermal image with a temperature intensity above the identified thermal threshold.

3. The method of claim 2, wherein a scale and orientation of the field of view of the thermal image is calibrated to align with the field of view of the color image, and wherein identifying the region of pixels in the color image corresponding to the first food item includes identifying the region of pixels in the color image corresponding to the at least one identified region of pixels corresponding to the one or more food items on the plate in the thermal image.

4. The method of claim 2, wherein analyzing the thermal image to identify the thermal threshold includes applying a window median method routine to the thermal image.

5. The method of claim 1, further comprising:
    identifying, by the electronic processor, a first region of pixels in the color image corresponding to a potential food item based at least in part on an edge finding routine applied to the color image by the electronic processor; and
    identifying, by the electronic processor, a second region of pixels in the thermal image corresponding to a potential food item based at least in part on the temperature intensity of the pixels in the second region of pixels relative to other pixels in the thermal image,
    wherein a scale and orientation of the field of view of the thermal image is calibrated to align with the field of view of the color image, and
    wherein identifying the region of pixels in the color image corresponding to the first food item based at least in part on the temperature intensity of the pixels in the identified region of pixels relative to other pixels in the thermal image includes
        determining, by the electronic processor, whether the first region of pixels in the color image corresponds to the first food item based at least in part on an alignment of at least some of the pixels in the first region of pixels in the color image with the second region of pixels in the thermal image.

6. The method of claim 1, further comprising applying an iterative segmentation refining routine to the identified region of pixels until a refined identified region of pixels output by the iterative segmentation refining routine converges.

7. The method of claim 6, wherein applying the iterative segmentation refining routine includes applying a GrabCub routine to the color image with a region of pixels identified based on temperature intensity in the thermal image as an initial region of interest.

8. The method of claim 1, wherein positioning two identifiable calibration targets near the food item includes placing a first bottle cap filled with cold water near the food item and placing a second bottle cap filled with cold water near the food item on a side of the food item opposite the first bottle cap.

9. The method of claim 1, further comprising:
analyzing, by the electronic processor, the identified region of pixels in the color image corresponding to the first food item to extract a plurality of feature vectors including at least one selected from a group consisting of a color feature vector, a texture feature vector, and a histogram of gradients feature vector;
applying, by the electronic processor, a machine learning routine to identify the type of food based on the plurality of extracted feature vectors and previously stored feature vector information corresponding to previously identified food items in a food item database; and
updating the food item database based on the plurality of extracted feature vectors for the first food item.

10. A food identification system comprising:
a color camera;
a thermal camera; and
an electronic processor configured to
receive a color image from the color camera with a first food item in a field of view of the color image,
receive a thermal image from the thermal camera with the first food item in a field of view of the thermal image,
identify a region of pixels in the color image corresponding to the first food item based at least in part on a temperature intensity of the pixels in the identified region of pixels relative to other pixels in the thermal image,
extract at least one feature from the identified region of pixels in the color image corresponding to the first food item, and
identify a type of food corresponding to the first food item based at least in part on the at least one extracted feature,
wherein the electronic processor is further configured to
identify a first calibration target and a second calibration target positioned in the field of view of the color image and in the field of view of the thermal image,
define a line in the thermal image extending from a defined location on the first calibration target to a defined location on the second calibration target,
define a line in the color image extending from the defined location on the first calibration target to the defined location on the second calibration target, and
adjust an orientation and a scale of the thermal image or the color image until a slope and size of the line in the thermal image matches a slope and size of the line in the color image.

11. The food identification system of claim 10, wherein the electronic processor is further configured to
analyze the thermal image to identify a thermal threshold indicative of a difference between a temperature of one or more food items on a plate and a temperature of the plate, wherein the one or more food items on the plate includes the first food item, and
identify at least one region of pixels corresponding to the one or more food items on the plate by identifying pixels in the thermal image with a temperature intensity above the identified thermal threshold.

12. The food identification system of claim 11, wherein a scale and orientation of the field of view of the thermal image is calibrated to align with the field of view of the color image, and wherein the electronic processor is configured to identify the region of pixels in the color image corresponding to the first food item by identifying the region of pixels in the color image corresponding to the at least one identified region of pixels corresponding to the one or more food items on the plate in the thermal image.

13. The food identification system of claim 10, wherein the electronic processor is further configured to
identify a first region of pixels in the color image corresponding to a potential food item based at least in part on an edge finding routine applied to the color image by the electronic processor, and
identify a second region of pixels in the thermal image corresponding to a potential food item based at least in part on the temperature intensity of the pixels in the second region of pixels relative to other pixels in the thermal image,
wherein a scale and orientation of the field of view of the thermal image is calibrated to align with the field of view of the color image, and
wherein the electronic processor is configured to identify the region of pixels in the color image corresponding to the first food item based at least in part on the temperature intensity of the pixels in the identified region of pixels relative to other pixels in the thermal image by determining whether the first region of pixels in the color image corresponds to the first food item based at least in part on an alignment of at least some of the pixels in the first region of pixels in the color image with the second region of pixels in the thermal image.

14. The food identification system of claim 10, wherein the electronic processor is further configured to apply an iterative segmentation refining routine to the identified region of pixels until a refined identified region of pixels output by the iterative segmentation refining routine converges.

15. The food identification system of claim 14, wherein the electronic processor is configured to apply the iterative segmentation refining routine by applying a GrabCub routine to the color image with a region of pixels identified based on temperature intensity in the thermal image as an initial region of interest.

16. The food identification system of claim 10, wherein the first calibration target includes a bottle cap filled with cold water positioned near the food item.

17. The food identification system of claim 10, wherein the electronic processor is further configured to analyze the identified region of pixels in the color image corresponding to the first food item to extract a plurality of feature vectors including at least one selected from a group consisting of a color feature vector, a texture feature vector, and a histogram of gradients feature vector, apply a machine learning routine to identify the type of food based on the plurality of extracted feature vectors and previously stored feature vector information corresponding to previously identified food items in a food item database, and update the food item database based on the plurality of extracted feature vectors for the first food item.

18. The food identification system of claim 10, further comprising a smart phone including the electronic processor, wherein the color camera includes a color camera built into the smart phone.

* * * * *